United States Patent
Shirota et al.

(10) Patent No.: US 10,070,833 B2
(45) Date of Patent: Sep. 11, 2018

(54) MOBILE X-RAY IMAGING APPARATUS

(71) Applicant: SHIMADZU CORPORATION, Kyoto (JP)

(72) Inventors: Ken Shirota, Kyoto (JP); Hiroshi Okumura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 181 days.

(21) Appl. No.: 15/124,213

(22) PCT Filed: Mar. 11, 2014

(86) PCT No.: PCT/JP2014/056367
§ 371 (c)(1),
(2) Date: Sep. 7, 2016

(87) PCT Pub. No.: WO2015/136627
PCT Pub. Date: Sep. 17, 2015

(65) Prior Publication Data
US 2018/0160992 A1     Jun. 14, 2018

(51) Int. Cl.
*A61B 6/00*     (2006.01)
*B62B 5/00*     (2006.01)
*G01P 13/00*     (2006.01)

(52) U.S. Cl.
CPC .......... *A61B 6/4405* (2013.01); *A61B 6/4452* (2013.01); *A61B 6/547* (2013.01); *A61B 6/587* (2013.01); *B62B 5/0069* (2013.01); *B62B 5/0033* (2013.01); *B62B 2202/00* (2013.01); *B62B 2301/044* (2013.01); *G01P 13/00* (2013.01)

(58) Field of Classification Search
CPC .................................................. A61B 6/4405
See application file for complete search history.

(56) References Cited

U.S. PATENT DOCUMENTS 5,351,282 A *   9/1994   Kadowaki ............ A61B 6/4405
                                                                               378/193
8,672,543 B2 *   3/2014   Kralles ................ A61B 6/4405
                                                                               378/102

FOREIGN PATENT DOCUMENTS

| JP | 05-128515 | 5/1996 |
| JP | 2002-45353 | 2/2002 |
| JP | 2004-350833 | 12/2004 |
| JP | 2005-224516 A | 8/2005 |

(Continued)

OTHER PUBLICATIONS

PCT/JP20141/056367, International Search Report dated Apr. 15, 2014, 1 page English, 3 pages Japanese.

*Primary Examiner* — Dani Fox
(74) *Attorney, Agent, or Firm* — Andrew F. Young, Esq.; Lackenbach Siegel, LLP

(57) ABSTRACT

A mobile X-ray imaging apparatus has an angle sensor and a movement calculation circuit that controls the driving of drive wheels based on the turning angle of auxiliary wheels relative to a straight moving direction of the base unit when a fine movement switch instructs movement of the base unit in the fine movement mode. The turning angle of auxiliary wheels is detected by a turning angle sensor and the rotation of the pair of drive wheels is controlled by the movement calculation circuit as the auxiliary wheels turns to the straight moving direction.

7 Claims, 12 Drawing Sheets

(56) References Cited

FOREIGN PATENT DOCUMENTS

| JP | 2010-046158 | 3/2010 |
| JP | 2010-094162 | 4/2010 |

\* cited by examiner

| Pressure Sensor 33a | Pressure Sensor 33b | Pressure Sensor 33c | Pressure Sensor 33d | Moving direction of base unit 3 | Turning direction of auxiliary wheel |
|---|---|---|---|---|---|
| ON | ON | OFF | OFF | Forward | Straight |
| OFF | OFF | ON | ON | Backward | Straight |
| OFF | ON | ON | OFF | Left turn | Left |
| ON | OFF | OFF | ON | Right turn | Right |

MOBILE X-RAY IMAGING APPARATUS

CROSS REFERENCE TO RELATED APPLICATIONS

This application relates to and claims priority from SN PCT/JP2014/056367 filed Mar. 11, 2014, the entire contents of which are incorporated herein by reference.

BACKGROUND OF THE INVENTION

Field of the Invention

The present invention relates to a mobile X-ray imaging apparatus for an X-ray imaging relative to a subject, and particularly relates to a mobile X-ray apparatus operable under a normal drive and operable along with a fine movement operation.

Description of the Related Art

In a medical practice, an X-ray imaging must be conducted in some cases by going around the patient who cannot be moved to the imaging room. In addition, an emergency X-ray imaging must be conducted in a surgical operation room in some cases. In such cases, as an apparatus for the X-ray imaging of the patient, a mobile X-ray imaging apparatus movable inside the hospital has been applied (e.g., Patent Document 1.)

Referring to FIG. 10, the inventor illustrates the structure of a conventional mobile X-ray imaging apparatus. Relative to the conventional example, a mobile X-ray imaging apparatus 101 comprises a base unit 103, a drive wheel 105, a front wheel 107, a mast 109, a boom 111, an X-ray tube 113 and a drive handle 115.

A pair of drive wheels 105 is mounted to the right-and-left side of the rear-bottom part of the base unit 103. The base unit 103 moves forward-and-backward following the rotation of the drive wheels 105 and turns to right-and-left depending on the difference of rotation rates between the right drive wheel 105 and the left drive wheel 105. The drive wheels 105 having an unturnable structure are configured rotatable by the electric motor installed inside the base unit 103. The front wheels 107 are mounted to the right-and-left side of the front-bottom of the base unit 103 and freely turnable depending on the turn direction of the base unit 103.

The mast 109 is mounted in the standing position at the front part of the base unit 103 and rotatable around the perpendicular axis. The one end of the boom 111 is connected to the mast 109. The boom is movable in the horizontal direction and the X-ray tube 113 is mounted to the other end, and a plurality of pressure sensors is installed inside the drive handle 115. The pressure sensors detect the pressure added to the driver handle 115 by the operator and the rotation of the drive wheels 105 is controlled based on the detected pressure.

When the mobile X-ray imaging apparatus 101 is applied, the operator moves to the patient room, where the X-ray imaging subject is present, along with the mobile X-ray imaging apparatus 101 while operating the drive handle 115. When moved in the patient room, referring to FIG. 11, the mast 109 and the boom 111 are appropriately moved to the optimal position to move the X-ray tube 113 for the X-ray imaging. And then, the X-ray is irradiated from the X-ray tube 113 to the subject M to take an X-ray image.

However, the X-ray tube 113 is supported by the base unit 103 through the mast 109 and the boom 111 so that the movable range of the X-ray tube 113 is limited relative to the base unit 103. Accordingly, when an appropriate imaging position relative to the subject is not in the movable range of the X-ray tube 113, the base unit 103 must be moved in an infinitesimal distance to perform fine adjustment of the position of the mobile X-ray imaging apparatus 101. In such case, if the base unit 103 is moved using the drive handle 115, the movement rate of the base unit 103 is high so that the fine adjustment of the position of the mobile X-ray imaging apparatus can be arduous. Accordingly, the move of the X-ray tube 113 to the appropriate imaging position can become problematic.

Accordingly and recently, referring to FIG. 10, a structure further including a fine movement switch 117 other than the drive handle 115 to perform a fine operation as to the base unit 103 is disclosed (e. g., Patent Document 2, 3.) When an operator operates the fine movement switch 117, the drive wheel 105 rotates a lower rate than in the case of the operation of the drive handle 115. The base unit 103 moves slightly in a low speed to forward or backward according to the rotation of the drive wheels 105 so that the fine adjustment of the position of the mobile X-ray imaging apparatus 101 can be performed. Hereinafter, the case when the drive wheels 105 are controlled by the operation of the drive handle 115 is described as "drive mode", and the case when the drive wheels 105 are controlled by the operation of the fine movement switch 117, which is described as "fine movement mode."

RELATED ART DOCUMENTS

Patent Document

Patent Document 1: JP 2010-46158 A1
Patent Document 2: JP 2002-45353 A1
Patent Document 3: JP 2004-350833 A1

ASPECTS AND SUMMARY OF THE INVENTION

Objects to be Solved

Nevertheless, in the case of a conventional example having such structure, the following problems remain to be solved.

Specifically, according to the conventional mobile X-ray imaging apparatus, the front wheel drive is turned to either right or left direction instead of the straight moving direction relative to the base unit in some cases. In such cases, when the fine movement switch is operated to initiate the fine movement, the base unit begins turning to right-and-left according to the turning direction of the front wheel and the move direction of the base unit cannot coincide with the straight moving direction of the base unit. Accordingly, the position adjustment of the mobile X-ray imaging apparatus can be difficult to follow the intended way.

Here, referring to FIG. 12., the inventor sets forth the detail of the problem of the conventional example, in which the front wheel 107 is turning to the left direction against the straight moving direction, indicated by the sign A, of the base unit 103. In such case, even if the drive wheel 105 is rotated forward by operating the fine movement switch 117 to move the base unit 103 with the fine movement mode in the direction A, the actual fine movement direction of the base unit 103 cannot be the direction A.

Because just after activated the fine movement mode, the front wheel 107 has turned to the left direction. Accordingly, even if a pair of the drive wheels 105 is rotated with the same speed, the base unit 103 moves toward the left front in the turn direction following the turn direction of the front wheel 107 for a constant time period after the fine movement is activated. Specifically, when the pair of the drive wheels 105 is rotated with the same rate, the base unit 103 moves from the position indicated by the solid line to the left front position indicated by the broken line.

Then, the base unit 103 turns toward left front for a constant time and while moving from the solid line position to the broken line position, the front wheels 107 gradually turns to the straight moving direction of the base unit 103 by the drive wheels 105 rotating with the same speed. According to the facing direction of the front wheels 107 turned to the straight moving direction of the base unit 103, the base unit 103 moves from the dot lined position in the straight moving direction and shifts to the position indicated by the dashed-two dotted line.

However, until the front wheels 107 turn to the straight moving direction of the base unit 103, the base unit 103 has moved toward left front in a constant distance. Accordingly, the base unit 103 moves from the solid line position toward the front left and until the dashed-two dotted line along the slightly S-curve orbit indicated the sign B. Specifically, when the front wheel 107 turns to the left direction, even if the base unit 103 is tried to be moved forward with a fine movement mode, the base unit 103 moves in the direction indicated by the sign B instead of i.e., the direction indicated by the sign A, which is the direction desired by the operator. As results, the base unit 103 moves slightly to the left compared to the position desired by the operator.

Further, when each drive wheel 105 is rotated backward at the same rate in order to move the base unit 103 backward at the fine movement mode, the base unit 103 turns toward left-back direction in accordance with a turning direction of the front wheel 107 for a constant time following the beginning of the fine movement operation and then backs straight backward. As results, the base unit 103 backs not in a right behind direction indicated by the sign C and instead, moves along the slightly S-curve orbit indicated by the sign D.

A movement in a fine movement mode requires an absolutely accurate control compared to a drive mode because the moving distance of the base unit 103 in the fine movement mode is in the range of approximately a few centimeters to a few ten centimeters. However, according to the conventional mobile X-ray imaging apparatus 101, after the fine movement switch 117 is operated, the base unit 103 turns in accordance with the turning direction of the front wheel 107 for a constant time. Accordingly, the fine adjustment of the position of the base unit 103 using the fine movement mode cannot be achieved with an absolute accuracy.

Considering such circumstances, the object of the present invention is to provide a mobile X-ray imaging apparatus capable of moving a base unit to the further accurate position in the fine movement mode, Means for Solving the Problem The present invention constitutes the following structure to solve such problem.

Specifically, a mobile X-ray imaging apparatus according to the present invention comprises; a base unit mounting an X-ray tube; a pair of drive wheels that is installed to the base unit, moves the base unit straight, and turns the same by being driven independently each other; auxiliary wheels that are installed to the base unit and turn following a turning movement of the base unit, a drive operation means that has an operation handle and conducts an operation of said base unit in the drive mode, wherein the pair of drive wheels can be rotated independently each other to move straight and turn the base unit based on an operation force added to the operation handle; a fine movement instruction means that specifies the movement of the base unit according to the fine movement mode, wherein the base unit is moved straight by rotating the drive wheels at the lower rotation rate than the rotation rate in the drive mode; an angle detection means that detects a turning angle of the auxiliary wheels relative to the straight moving direction of the base unit; a drive wheels control means to control independently each other the rotation rates of the pair of the drive wheels as the auxiliary wheels turn to the straight moving direction of the base unit based on the turning angle of the auxiliary wheels, which is detected by the turning angle detection means in the fine movement mode, of the auxiliary wheels.

A mobile X-ray imaging apparatus according to the present invention comprises the turning angle detection means and the drive wheels control means. The drive wheels control means controls independently each other the pair of drive wheels based on the turning angle of auxiliary wheels relative to the straight moving direction of the base unit when the fine movement instruction means instructs the movement of the base unit in the fine movement mode. The turning angle of the auxiliary wheels relative to the straight moving direction is detected by the turning angle detection means and the rotation rates of the pair of the drive wheels are controlled each independently by the drive wheels control means as the auxiliary wheels turns to the straight moving direction of the base unit. Therefore, even if the auxiliary wheels are turning to right-and-left in the drive mode, the auxiliary wheels quickly turn to the straight direction of the base unit by the drive wheels control means. The turning direction of the auxiliary wheels is corrected to the straight moving direction of the base unit so that the base unit can be avoided to turn to right-and-left according to the auxiliary wheels turning to right-and-left. Accordingly, the base unit can be moved accurately forward or backward in the fine movement mode and the position of the base unit can be adjusted as intended.

Further, according to the mobile X-ray imaging apparatus of the present invention, the turning angle detection means is preferably an angle sensor to detect the turning angle of the auxiliary wheels relative to the straight moving direction of the base unit.

According to the mobile X-ray imaging apparatus of the present invention, the turning angle detection means is the angle sensor to detect the turning angle of the auxiliary wheels relative to the straight moving direction of the base unit. The angle sensor directly detects the turning angle of the auxiliary wheels relative to the straight moving direction of the base unit so that the turning angle of the auxiliary wheels can be accurately detected. Accordingly, the drive wheels control means can control further accurately the rotation of the drive wheels to shift the turning angle of the auxiliary wheels to the straight moving direction of the base unit.

Further, it is preferred that the mobile radiographic device of the present invention comprises; the turning angle detection means comprising a turning angle calculation means to calculate the turning angle of the auxiliary wheels to the straight moving direction of the base unit as needed, and a turning angle storing means to store the turning angle of the auxiliary wheels to the straight moving direction of the base unit; and the drive wheels control means controlling independently each other the rotation rates of the pair of the drive wheels based on the turning angle, which is stored in the turning angle storing means, of the auxiliary wheels relative to the straight moving direction of the base unit.

A mobile X-ray imaging apparatus according to the present invention comprises a turning angle detection means and the drive wheels control means. The turning angle calculation means calculates the turning angle of the auxiliary wheels relative to the straight moving direction of the base unit as needed and the calculated turning angle is stored in the turning angle storing means as needed. Then, the drive wheels control means controls independently each other the rotation rates of the pair of the drive wheels based on the turning angle, which is stored by the turning angle storing means, of the auxiliary wheels relative to the straight moving direction of the base unit. Accordingly, the base unit can be moved accurately forward or backward in the fine movement mode and the position of the base unit can be adjusted as intended.

Further, the turning angle calculation means and the turning angle storing mean are configured with software. Specifically, the turning angle detection means requires newly no additional hardware such as an angle sensor and so forth to detect the turning direction of the auxiliary wheels. Accordingly, the manufacturing processes for the mobile X-ray imaging apparatus and the design thereof require no significant modification. Accordingly, while the manufacturing cost for the mobile X-ray image apparatus is being saved, the rotation rates of the pair of drive wheels can be controlled independently each other as the base unit slightly moves toward the straight moving direction in the fine movement mode.

Further, the mobile X-ray imaging apparatus according to the present invention preferably further comprises a rotation angle detection means to detect the rotation rate of the drive wheels and a rotation direction as needed and the turning angle calculation means calculates the turning angle of the auxiliary wheels relative to the straight moving direction of the base unit based on the rotation rate and the rotation direction of the drive wheels detected by the rotation detection means as needed.

A mobile X-ray imaging apparatus according to the present invention comprises a rotation detection means to detect the rotation rate and the rotation direction of the drive wheels as needed. And then, the turning angle calculation means calculates the turning angle of the auxiliary wheels relative to the straight moving direction of the base unit based on the rotation rate and the rotation direction of the drive wheels detected by the rotation detection means as needed.

The auxiliary wheels turns according to the turning direction of the base unit as needed, and the rotation direction of the base unit is determined by the rotation rate and the rotation direction of the drive wheels. Accordingly, the turning angle of the auxiliary wheels relative to the straight moving direction of the base unit can be calculated based on the rotation rate and the rotation direction of the drive wheels. Accordingly, the base unit can be moved accurately forward or backward in the fine movement mode and the position of the base unit can be adjusted as intended.

Further, according to the mobile X-ray imaging apparatus of the present invention, the turning angle calculation means preferably calculates the turning angle of the auxiliary wheels relative to the straight moving direction of the base unit based on the pressure detected by an pressure sensor installed to the drive handle.

According to the mobile X-ray imaging apparatus of the present invention, the turning angle calculation means calculates the turning angle of the auxiliary wheels relative to the straight moving direction of the base unit based on the pressure detected by the pressure sensor installed to the drive handle. The auxiliary wheels turns following the turning direction of the base unit as needed. Then, the rotation rate and the rotation direction are controlled by the pressure detected by the pressure sensor installed to the operation handle, and the turning direction is determined by the rotation rate and the rotation direction of the drive wheels. Specifically, the turning direction of the auxiliary wheels relative to the straight moving direction of the base unit based on the pressure detected by the pressure sensor as needed. Accordingly, the base unit can be moved accurately forward or backward in the fine movement mode and the position of the base unit can be adjusted as intended by detecting the pressure which the pressure sensor detects as needed.

In addition, a mobile X-ray imaging apparatus according to the present invention further preferably comprises a mode discrimination means that discriminates the drive mode and the fine movement mode, and switches the on-and-off control of rotation rates of the pair of the drive wheels by the drive wheel control means based on the discrimination result.

According to the mobile X-ray imaging apparatus of the present invention, the mode discrimination means discriminates the drive mode and the fine movement mode, and switches the on-and-off control of rotation rates of the pair of the drive wheels by the drive wheel control means based on the discrimination result. Specifically, the mode discrimination means discriminates the fine movement mode so that the drive wheel control means can control the rotation rates of the pair of the drive wheels independently each other as the auxiliary wheels turn to the straight moving direction of the base unit.

On the other hand, when the mode discrimination means discriminates the drive mode, the drive wheel control means switches the on-and-off control of the rotation rates of the pair of the drive wheels by the drive wheel control means as the drive wheel control means would not control the rotation rate of the drive wheels. Accordingly, it can be adequately avoided that the control of the drive wheel control means is mistakenly performed in the drive mode so as to turn the turning direction of the auxiliary wheels to the straight moving direction of the base unit. Accordingly, the base unit can be moved accurately forward or backward in the fine movement mode and the position of the base unit can be more assuredly adjusted as intended.

Effect of the Invention

A mobile X-ray imaging apparatus according to the present invention comprises a turning angle detection means and the drive wheels control means. The drive wheels control means controls independently each other the pair of drive wheels based on the turning angle of auxiliary wheels relative to the straight moving direction of the base unit when the fine movement instruction means instructs the movement of the base unit in the fine movement mode. The turning angle of the auxiliary wheels relative to the straight moving direction is detected by the turning angle detection means and the rotation rates of the pair of the drive wheels are controlled independently each other by the drive wheels control means as the auxiliary wheels turns to the straight moving direction of the base unit. Therefore, even if the auxiliary wheels are turning to right-and-left in the drive mode, the auxiliary wheels quickly turn to the straight moving direction of the base unit by the drive wheels control means. The turning direction of the auxiliary wheels is corrected to the straight moving direction of the base unit so that the base unit can be avoided to turn to right-and-left according to the auxiliary wheels turning to right-and-left. Accordingly, the base unit can accurately move forward or backward in the fine movement mode and the position of the base unit can be adjusted as intended.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 3A is a plan view illustrating the structure of the pressure sensor, and FIG. 3B is a table illustrating the relationship a combination of pressure sensors, which detect pressures, and an operation of the base unit and the auxiliary wheels.

FIG. 6A is before control of the turning direction of the auxiliary wheels, FIG. 6B is under control of the turning direction of the auxiliary wheels, and FIG. 6C is after control of the turning direction of the auxiliary wheels.

DETAILED DESCRIPTION OF THE PREFERRED EMBODIMENTS

Figure 1:
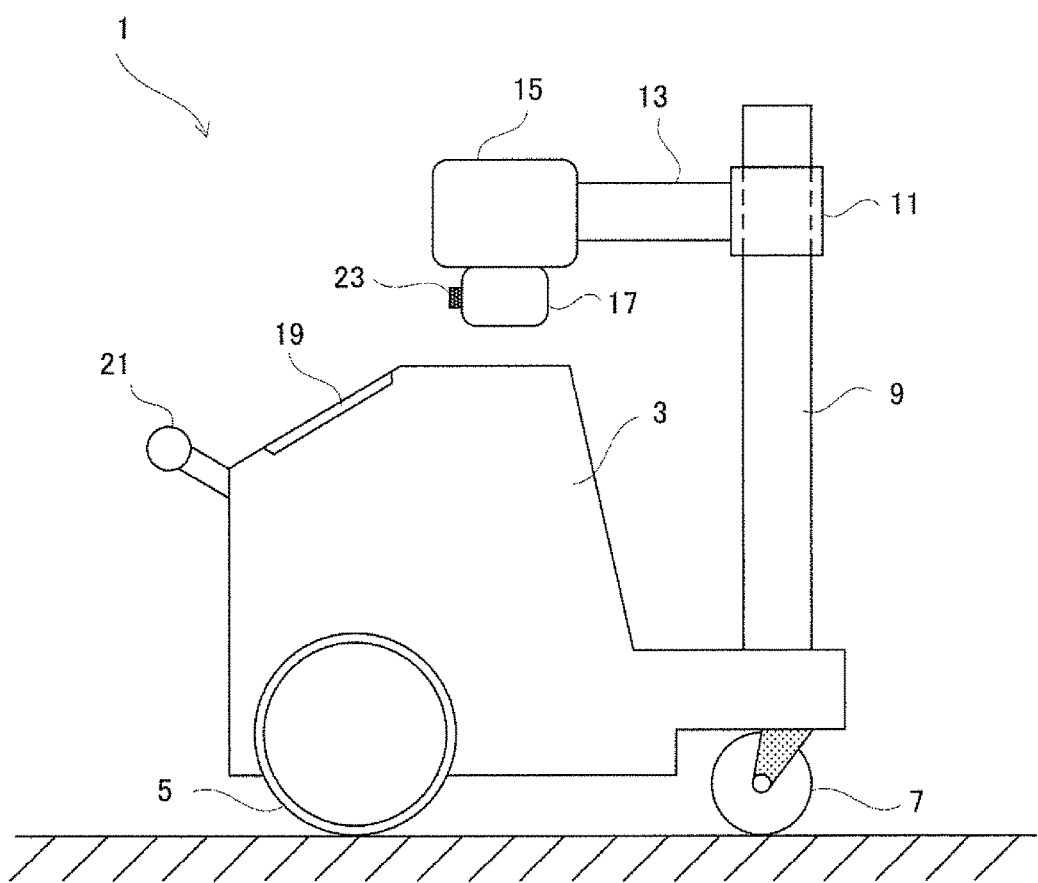
FIG. 1 is a left side view illustrating the structure of a mobile X-ray imaging apparatus of the Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Embodiment 1

Referring to FIGs, the inventor sets forth the Embodiment 1 of the present invention. FIG. 1 is a left side view illustrating the structure of the mobile X-ray imaging apparatus of the Embodiment 1.

Illustration of the Entire Structure

According to the Embodiment 1, a mobile X-ray imaging apparatus 1 comprises a base unit 3, a drive wheel 5, a front wheel 7, a mast 9, a support element 11, a boom 13, an X-ray tube 15, a collimator 17, a input element 19, a drive handle 21, and a fine movement switch 23.

A pair of drive wheels 5, which rotate by a motor set forth later, is mounted to the right-and-left side of the rear-bottom part of the base unit 3. The base unit 3 moves forward-and-backward following the rotation of the drive wheels 5 and turns to right-and-left depending on the difference of the rotation rates between the right and left drive wheels 5. A pair of front wheels 7 is mounted to the right and left sides of the front-bottom part of the base unit 3. The auxiliary wheels 7 are, e.g. a pair of casters, turn to right-and-left following the turning movement of the base unit 3.

The mast 9 are mounted upright at the front part of the base unit 3 and configured to be rotatable around the perpendicular axis. The support element 11, which is movable up-and-down along the mast 9, is mounted to the mast 9. In addition, the one end of the doom 13 is connected to the support element 11. The boom 13 is configured to be movable in the horizontal direction along the support element 11. The X-ray tube is mounted to the other end of the boom 13 and irradiates an X-ray.

The collimator 17 installed below the X-ray tube 15 limits X-rays irradiated from the X-ray tube 15 to a pyramid-like cone shape. In addition, an illumination light, not shown in FIG., is mounted to the collimator 17. Then, when the illumination light is lit up, the incident area of the X-rays limited by the collimator 17 is lit with the visible light. The input element 19 is installed to the rear side of the base unit 3 and may include e.g., a touch panel input device or a input keyboard. The operator sets the imaging conditions and so forth for an X-ray imaging by operating the input element 19.

The drive handle 21 is installed to the rear part of the base unit 3. The operator can controls the rotation of the drive wheels 5 by operating the drive handle 21. The fine movement switch 23 is a switch as a button type, a joy-stick type and so forth, and is configured to instruct the forward-and-backward moving of the base unit 3. The operator can rotate the drive wheels 5 at a low speed to move slightly the base unit forward or backward by operating the fine movement switch 23. Further, it is preferred that the fine movement switch 23 should be mounted to the X-ray tube 15 or the collimator 17 as the operator can conduct such fine movement operation while adjusting the position of the X-ray tube 15. According to the Embodiment 1, the fine movement switch 23 is deemed mounted to the collimator 17. The drive handle 21 corresponds to the driving operation means of the present invention and the fine movement switch 23 corresponds to the fine movement operation instruction means of the present invention.

Figure 2:
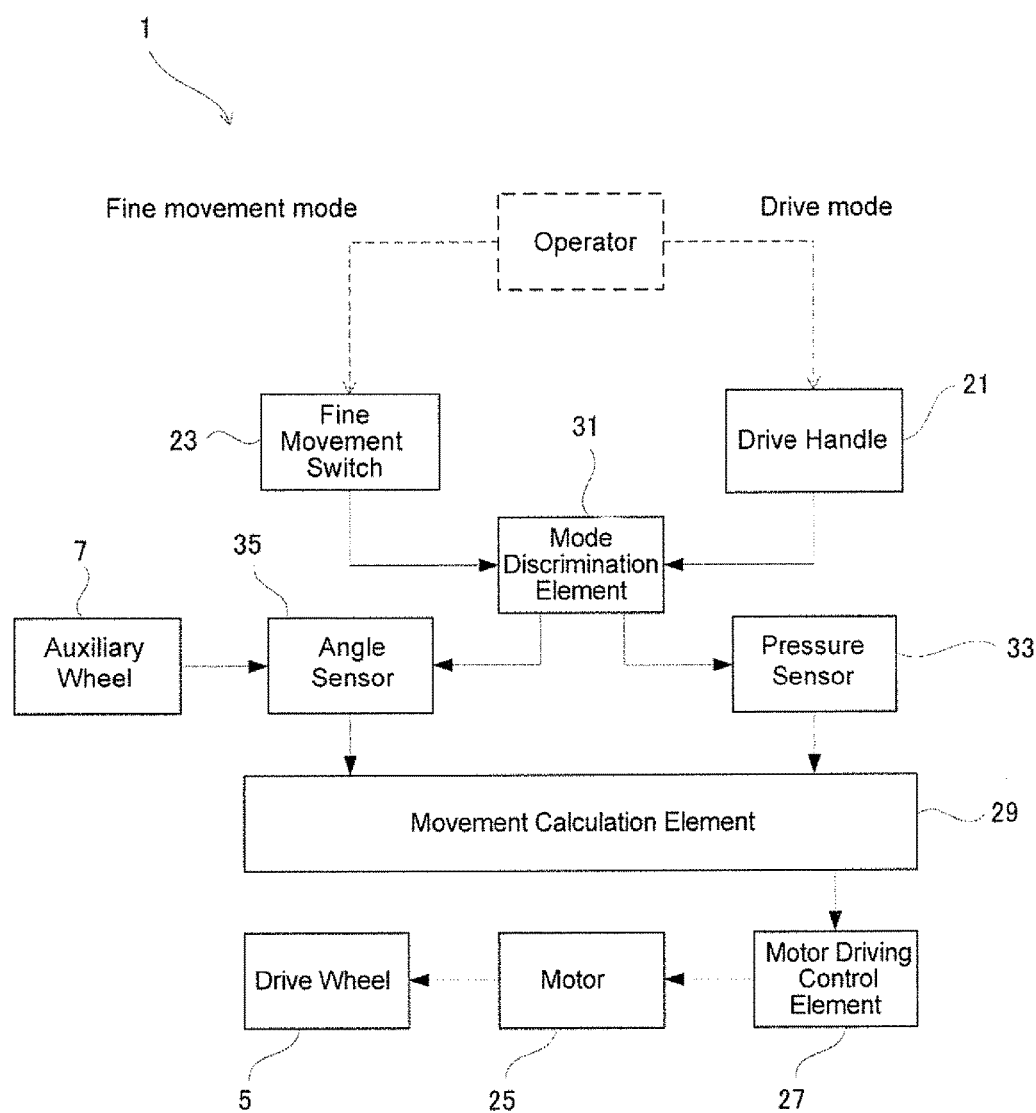
FIG. 2 is a functional block diagram illustrating a mobile X-ray imaging device of the Embodiment 1.

In addition, referring to FIG. 2, the mobile X-ray imaging apparatus 1 according to the Embodiment 1, a motor 25 is connected to each drive wheel 5. Then, each drive wheel 5 is configured to be rotated or halted independently by the motor 25. The rotation rate of each motor 25 is controlled by the motor driving control element 27. A movement calculation circuit 29 is installed in the front part of the motor driving control element 27 and calculates the rotation rate and the rotation direction of each drive wheel 5 respectively.

The data calculated by the movement calculation circuit 29 relative to the rotation rate and the rotation direction of the drive wheels 5 are sent to the motor driving control element 27. The motor driving control element 27 controls each drive of the motor 25 according to the data calculated by the movement calculation circuit 29. The motor driving control element 27 and the movement calculation circuit 29 correspond to the drive wheel control means of the present invention.

The mode discrimination element 31 discriminates the case when the operator is operating the drive handle 21 (drive mode) and the case when the operator is operating the fine movement switch 23 (fine movement mode.) Then, the mode discrimination element 31 sends alternatively the control signal to the pressure sensor 33 or the angle sensor 35 based on the discriminated result. Specifically, the mode discrimination element 31 sends control signal to the pressure sensor 33 relative to the drive mode and sends control signal to the angle sensor 35 relative to the fine movement mode. Further, the mode discrimination element 31 corresponds to the mode discrimination means of the present invention.

A plurality of the pressure sensors 33 is installed to the drive handle 21. Each pressure sensor 33 detects the pressure added to the drive handle 21 by the operator in the drive mode. Then, each sensor 33 corresponds to the control signal received from the mode discrimination element 31 and then sends the detected pressure data to the movement calculation circuit 29.

The angle sensor 35 is installed to each auxiliary wheel 7 respectively so that each turning angle of the auxiliary wheels 7 relative to the base unit 3 can be detected as needed. Then, each angle sensor 35 corresponds to the control signal received from the mode discrimination element 31 and sends the detected turning angle data to the movement calculation circuit 29. As an example of the angle sensor 35, a rotary encoder and a potentiometer and so forth can be included.

Figures 3A, 3B:
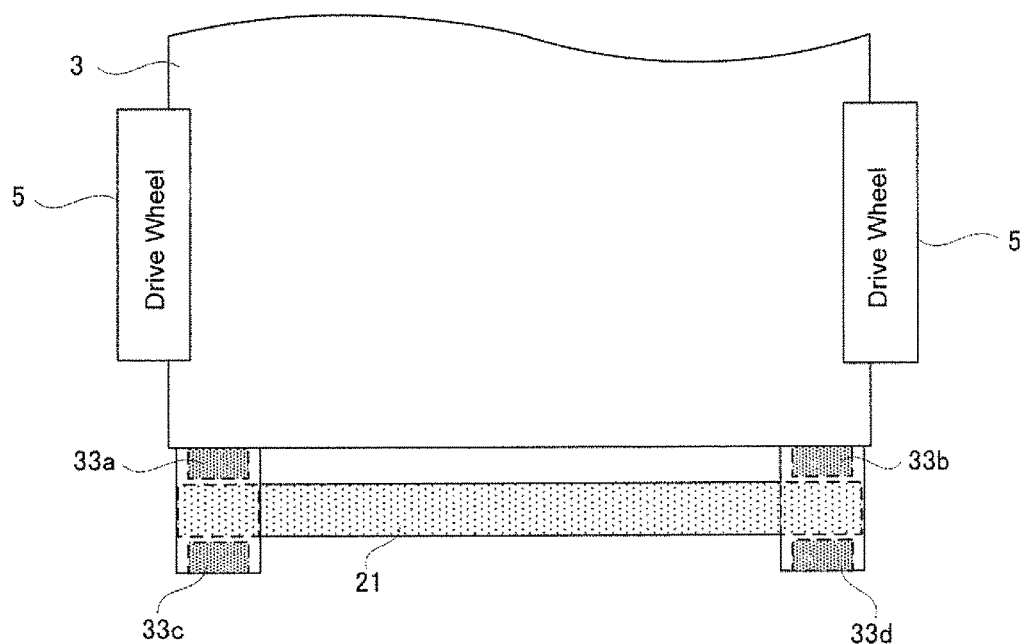
FIGS. 3A and 3B are views illustrating a structure of a pressure sensor according to the Embodiment 1.

Here, referring to FIG. 3A, the inventor sets forth the structure of the pressure sensor 33 installed to the drive handle 21. The pressure sensor 33 consists of four pressure sensors 33a-33d. The pressure sensor 33a is installed to the left side of the front of the drive handle 21 and the pressure sensor 33b is installed to the right side of the front thereof. The pressure sensor 33c is installed to the left side of the rear of the drive handle 21 and the pressure sensor 33d is installed to the right side of the rear thereof.

When the operator grips the drive handle 21 by both hands to try to move straight the base unit 3 and pushes both sides of the drive handle 21 forward, the pressures added to the drive handle 21 are detected by the pressure sensor 33a and the pressure sensor 33b. The detected pressure data is sent to the movement calculation circuit 29 from the pressure sensor 33 based on the control signal that the mode discrimination element 31 sends. The movement calculation circuit 29 outputs the control signal to the motor driving control element 27 based on the combination of the control signal which are sent.

The motor control element 27 drives each motor 25 respectively as any wheels of the pair of the drive wheels 5 rotates at the same speed based on the control signal. The drive wheels 5 rotate forward at the same speed so that the base unit 3 can move forward (FIG. 3(b), the second row.) On the other hand, when the base unit need to move backward, both right side and left side of drive handle 21 are pulled. At this time, the pressure added to the drive handle 21 is detected by the pressure sensor 33c and the pressure sensor 33d. Then, any wheels of the pair of drive wheels 5 are controlled to rotate backward at the same rate and the base unit 3 moves backward (FIG. 3B: the third row.)

Further, when the operator turns the base unit 3 to the left in the drive mode, the left side of the drive handle 21 is pulled and the right side of the drive handle 21 is pushed forward. At this time, the pressures added to the drive handle 21 are detected by the pressure sensor 33b and the pressure sensor 33c. The detected pressure data is sent to the movement calculation circuit 29 from the pressure sensor 33. The movement calculation circuit 29 outputs the control signal to the motor driving control element 27 based on the control signal.

The motor control element 27 drives each motor 25 respectively based on the control signal as the rotation rate of the right wheel of the drive wheels 5 becomes faster than the left wheel of the drive wheels 5. As results, the base unit 3 turns to the left direction (FIG. 3B:the fourth row.) At such case, the turning direction of each auxiliary wheel 7 changes to the left direction following the movement direction of the base unit 3.

On the other hand, when the operator turns the base unit 3 to the right direction in the drive mode, the left side of the drive handle 21 is pushed forward and the right side of the drive handle 21 is pulled backward. At this time, the pressure added to the drive handle 21 are detected by the pressure sensor 33a and the pressure sensor 33d and the rotation rate of the left wheel of the drive wheels 5 is controlled to become faster than the right wheel of the drive wheels 5 (FIG. 3B: the fifth row.) At such case, the turning direction of each auxiliary wheel 7 changes to the right direction following the movement direction of the base unit 3.

Detail Description of the Operation

Figure 4:
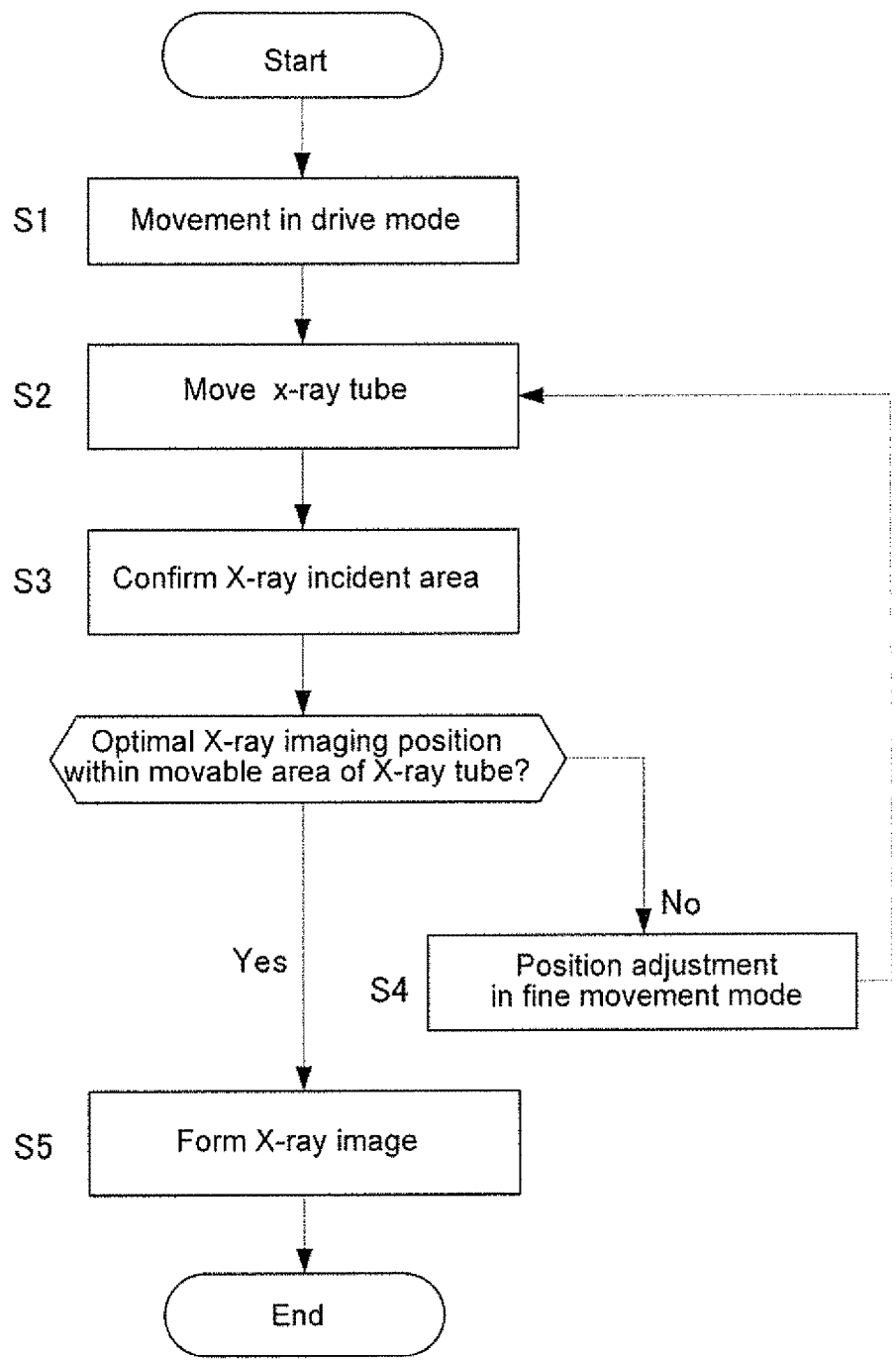
FIG. 4 is a flow chart illustrating an operation of the mobile X-ray imaging apparatus of the Embodiment 1.
Figure 5:
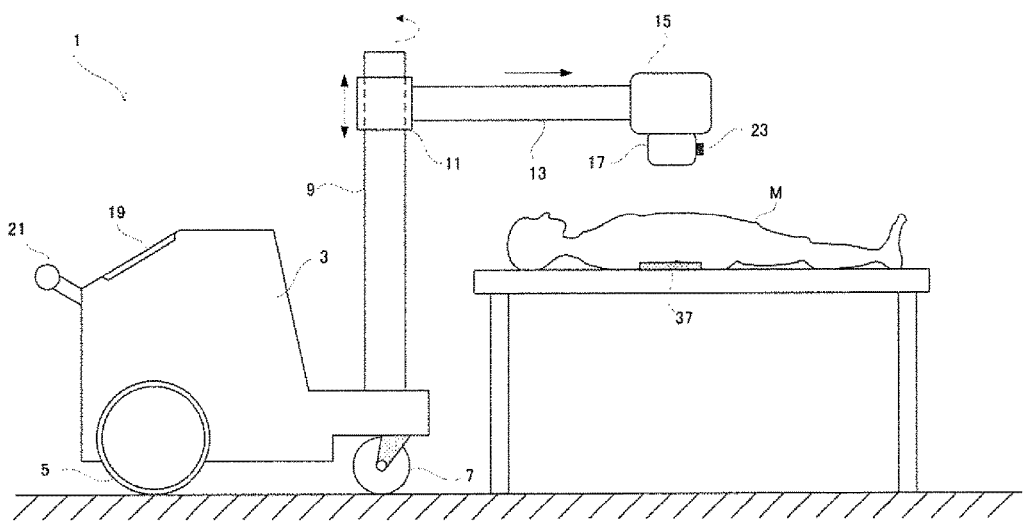
FIG. 5 is a schematic diagram illustrating a process of the Step S2 relative to the mobile X-ray imaging apparatus of the Embodiment 1.

Referring to FIGs., the inventor sets forth one example of the operation relative to a mobile X-ray imaging apparatus having the above described configuration. FIG. 4 is a flow chart illustrating an operation of the Embodiment 1.

Step S1 (Movement in the Drive Mode

First, the operator moves the mobile X-ray imaging apparatus 1 in the drive mode to the patient's room where the subject is present. When the operator contacts the drive handle 21 to move the base unit 3 in the drive mode, the contact sensor, not shown in FIG., installed to the drive handle 21 detects the operator's contact thereto. A signal is sent to the mode discrimination element 31 due to the detection by the contact sensor. The mode discrimination element 31 discriminates the drive mode based on the signal received therefrom. If the drive mode per se is discriminated, the mode discrimination element 31 sends the control signal to the pressure sensor 33.

Each pressure sensor 33 respectively detects the pressure added to the drive handle 21 by the operator in the drive mode. The detected pressure data are sent to the movement calculation circuit 29 from each pressure sensor 33. The movement calculation circuit 29 calculates the appropriate rotation rate and the rotation direction relative to each drive wheel 5 based on the received control signal and outputs the control signal to the motor driving control element 27.

The motor control element 27 drives each motor 25 respectively based on the control signal and respectively rotates each drive wheel 5. The base unit 3 moves in the direction intended by the operator according to rotation of the drive wheel 5. The operator operates the drive handle 21 by both hands and moves the mobile X-ray imaging apparatus 1 in the drive mode to the patient's room where the subject is present.

Step S2 (Movement of the X-Ray Tube)

After the operator moved into the patient's room with the mobile X-ray imaging apparatus 1, the operator takes out an X-ray detector 37 from the storage therefor (not shown in FIG.) and set the X-ray detector 37 between the imaging region of the subject M and the bed thereof. Then, the X-ray tube 15 is moved following the setup of the X-ray detector. Specifically, the mast 9 pivots around perpendicular axis and the support element 11 is moved in the up-and-down direction and the boom is moved in the horizontal direction, appropriately. The X-ray tube 15 moves along with movements of the mast 9, the support element 11 and the boom 13 over the subject M.

Step S3 (Confirmation of the X-Ray Incident Area)

After the X-ray tube 15 is moved, the X-ray incident area should be confirmed. Specifically, the operator tunas on the illumination light to emit the visible light through the collimator to illuminate the X-ray incident area of the subject M. Then, the positioning of the X-ray tube 15 to take a suitable X-ray image relative to the subject M is conducted using the illuminated X-ray incident area as a benchmark.

However, the X-ray tube 15 is supported by the base unit 3 through the mast 9, the support element 11 and the boom 13 so that the movable range of the X-ray tube 15 can be limited relative to the base unit 3. Accordingly, the optimal position for X-ray imaging relative to the subject M may be out of the movable range of the X-ray tube 15. In such case, the position adjustment of the base unit 3 is performed in the fine movement mode in association with the Step 4.

Step S4 (Position Adjustment in the Fine Movement Mode)

When the position of the base unit 3 is adjusted in the fine movement mode, the operator operates the fine movement switch 23. A signal is sent from the fine movement switch 23 to the mode discrimination element 31 by operating the fine movement switch 23. The mode discrimination element 31 discriminates the drive mode based on the received signal and sends the control signal to the angle sensor 35.

The angle sensor 35 detects the turning angle of the auxiliary wheels 7 relative to the base unit 3 as needed so that the data of detected turning angle can be sent to the movement calculation circuit 29 as needed based on the control signal received from the mode discrimination element 31. The movement calculation circuit 29 calculates the rotation rate and the rotation direction of the drive wheel 5 as the base unit 3 moves slightly to the straight moving direction based on the data received from the angle sensor 35. Further, in the fine movement mode, the movement calculation circuit 29 controls as the rotation rate of the drive wheel 5 is low compared to the rotation rate of the drive wheel 5 in the drive mode.

Figure 6A:
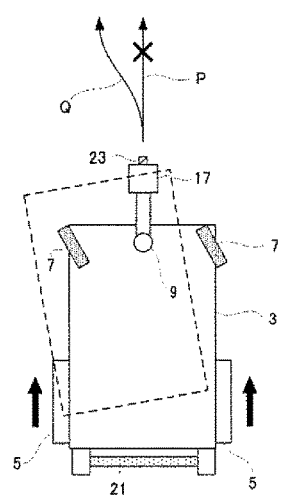
FIGS. 6A, 6B, and 6C are schematic diagrams illustrating a process of the Step S4 relative to the mobile X-ray imaging apparatus of the Embodiment 1. Respectively.
Figure 6B:
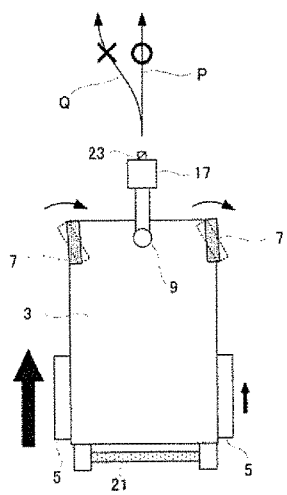
Figure 6C:
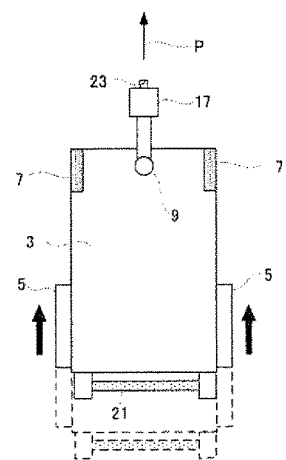

Here, referring to FIG. 6A, 6B, 6C, the inventor sets forth specifically the drive control mechanism of the base unit 3 in the fine movement mode in the case of the auxiliary wheels 7 turning to the left direction relative to the straight moving direction of the base unit 3. Further, the straight moving direction of the base unit 3 is indicated by the sign P this time.

In such case, even if the right-and-left drive wheels 5 rotates at the same rotation speed to move the base unit 3 straight in the direction P, the fine movement direction of the base unit 3 is not in the direction P. Because the base unit 3 turns to the left direction following the turning direction of the auxiliary wheels 7. Accordingly, the base unit 3 turns to the left direction relative to the straight moving direction P. Then, the auxiliary wheels 7 gradually turns to the straight moving direction of the base unit 3 by the drive wheels 5 rotating at the same speed.

However, when the auxiliary wheels 7 turns to the straight moving direction of the base unit 3, the straight moving direction of the base unit 3 already is changed to the left direction relative to the direction P. Accordingly, the base unit 3 moves to the straight moving direction after turning to the left relative to the direction P for a constant time. Specifically, the actual moving direction of the base unit 3 moving slightly at a low speed is not the direction P intended by the operator but instead, the direction indicated by the sign Q, which is toward left front direction as drawing the slightly S-curve orbit.

Then, the movement calculation circuit 29 calculates the rotation rate and the rotation direction of the drive wheels 5 and a control signal to the motor drive control element 27 to quickly correct the turning direction of the auxiliary wheels 7 to the straight moving direction of the base unit 3. At this time, the mode discrimination element 31 discriminates as the fine movement mode so that the movement calculation circuit 29 calculates the rotation rate of each drive wheel 5 as lower than in the drive mode. Then, the movement calculation circuit 29 calculates the rotation rate of the left drive wheel 5 so as to be larger than the rotation rate of the right drive wheel 5.

Figure 7:
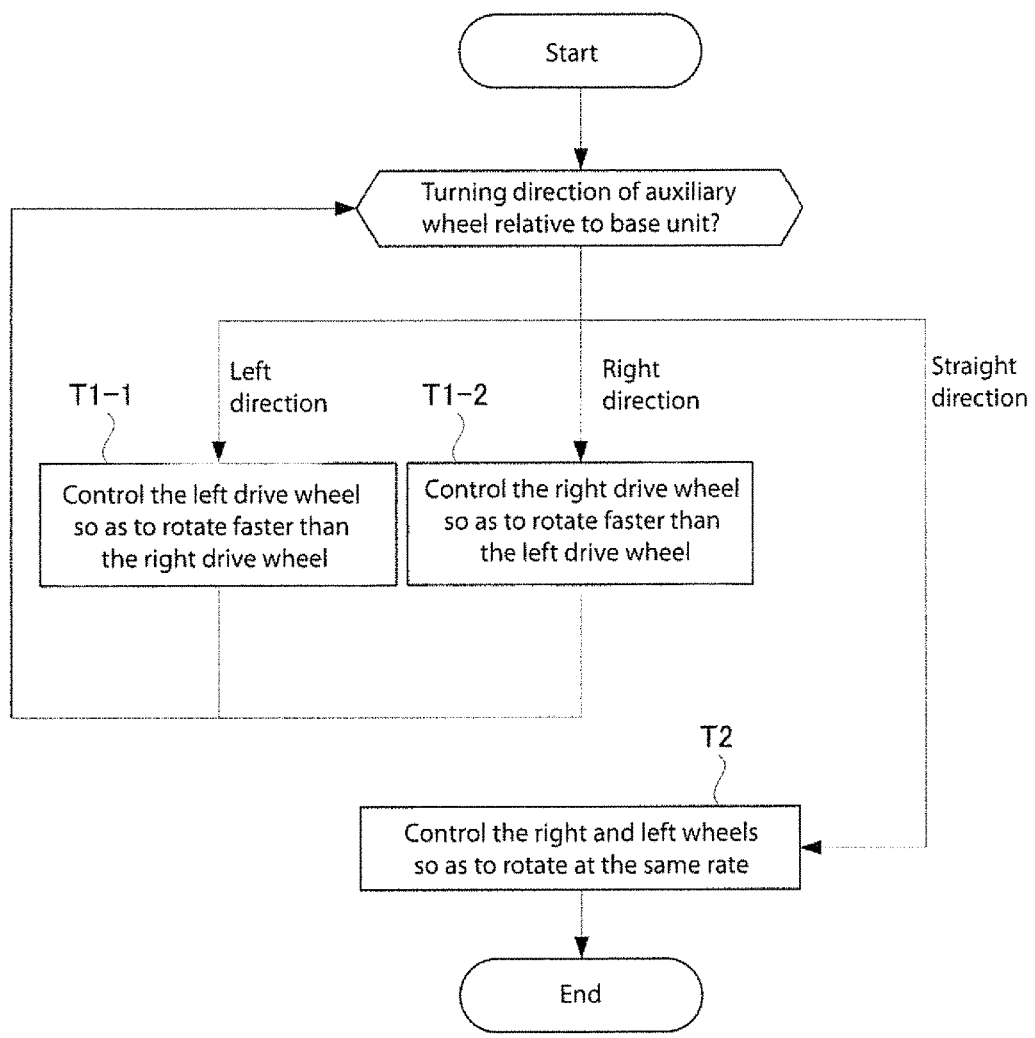
FIG. 7 is a flow chart illustrating the control mechanism of the drive wheels, in which the mobile calculation circuit relative to the Step S4 executes.

The motor control element 27 drives each motor 25 respectively based on the control signal as the rotation rate of the right wheel of the drive wheels 5 becomes faster than the left wheel of the drive wheels 5 (FIG. 7, sign T1-1.) Then, the turning direction of the auxiliary wheels 7 change quickly to the right according to the difference of the rotation rates of the right and left wheels 5. As results, the turning direction of the auxiliary wheels 7, which is left direction relative to the straight moving direction of the base unit 3, changes quickly to the straight moving direction of the base unit 3 (FIG. 6B.)

When the auxiliary wheels 7 turn to the straight moving direction of the base unit 3, the angle sensor 35 detects the changed turning angle of the auxiliary wheels 7 and the data related to the turning angle to the movement calculation circuit 29. The movement calculation circuit 29 recalculates the appropriate rotation rate and rotation direction of the drive wheels 5 based on the received control signal and outputs the control signal to the motor driving control element 27. At this time, any rotation rates of the drive wheels 5 recalculated by the movement calculation circuit 29 are the same.

The motor control element 27 controls each motor 25 respectively based on the control signal as the rotation rate of the right-and-left wheels of the drive wheels 5 rotate at the same speed (FIG. 7, sign T2.) The base unit 3 moves slightly at a low rate to the direction P, which is the straight moving direction, according to the drive wheels 5 rotating at the same speed and the auxiliary wheels 7 facing the straight moving direction (FIG. 6C.) Due to such configuration, the operator can move the base unit 3 to the direction P at a low rate as intended by the operator in the fine movement mode.

In addition, the movement calculation circuit 29 calculates the rotation rate and the rotation direction of the drive wheels 5 based on the data received from the angle sensor 35 when the auxiliary wheels 7 turns to the right direction relative to th base unit 3. Then, the calculated data are sent to the motor driving control element 27. The motor control element 27 controls each motor 25 respectively to drive based on the received signal as the rotation rate of the right wheel of the drive wheels 5 becomes faster than the left wheel of the drive wheels 5 (FIG. 7, sign T1-2.) Then, the turning direction of the auxiliary wheels 7 change quickly to the left according to the difference of the rotation rates of the right and left wheels 5. As results, the turning direction of the auxiliary wheels 7 which is the right direction relative to the straight moving direction of the base unit 3, changes quickly to the straight moving direction of the base unit 3. According to such control mechanism, the base unit 3 can be moved straight as intended and the position of the base unit 3 can be adjusted to be in-place in the optimal position for the X-ray imaging.

After adjustment of the position of the base unit 3, the operator move again the X-ray tube 15 in association with the Step S2 and confirms the X-ray incident area in association with the Step S3. Then, after the operator moves the position of the X-ray tube 15 to the optimal position for the X-ray imaging and confirms that the X-ray incident position and area thereof are appropriate, the process in association with the Step S5 is executed.

Step S5 (Formation of an X-Ray Image)

The operator turns off the illumination light and erases the X-ray incident area indicated by the visual light. Then, the operator sets up the predetermined conditions for the X-ray imaging by operating the operation panel 19. The operator irradiates X-ray from the X-ray tube 15 by operating the operation panel 19 following setting up the appropriate X-ray imaging conditions.

The X-ray irradiated from the X-ray tube 15 that transmits the imaging region of the subject M is detected by the X-ray detector 37 and output as the detected X-ray signal. Then, an X-ray image is formed based on the detected X-ray signal output therefrom and the formed X-ray image therefrom is displayed on the operation panel 19. The operator confirms the displayed X-ray image and ends the X-ray imaging by operating the operation panel 19. After the imaging, the operator recovers the X-ray detector 37, operates the drive handle 21, gets out of the patient's room with the mobile X-ray imaging apparatus 1 and then moves to a next location.

(Effects of the Configuration According to the Embodiment 1)

A mobile X-ray imaging apparatus according to the Embodiment 1 comprises the angle sensor 35 so that the turning angle of the auxiliary wheels 7 relative to the base unit 3 can be detected as needed. Further, in the fine movement mode, a signal is sent from the fine movement switch 23 to the mode discrimination element 31 by operating the fine movement switch 23. The mode discrimination element 31 discriminates the fine movement mode based on the signal that was sent therefrom and sends the control signal to the angle sensor 35. Then, the angle sensor 35 corresponds to the control signal received sent from the mode discrimination element 31 and sends the detected turning angle data of the auxiliary wheels 7 to the movement calculation circuit 29.

The movement calculation circuit 29 calculates the rotation rate and the rotation direction of each drive wheel 5 as the turning direction of the auxiliary wheels 7 is changed quickly to the straight moving direction of the base unit 3 based on the data received from the angle sensor 35. The turning direction of the auxiliary wheels 7 changes quickly to the straight moving direction of the base unit 3 in the fine movement mode so that the turning direction of the auxiliary wheels 7 can be quickly the straight moving direction of the base unit 3 right after the initiation of the fine movement of the base unit 3.

Then, according to the turning direction of the auxiliary wheels 7 changing to the straight moving direction, the base unit 3 moves slightly to the straight moving direction. Specifically, even when the auxiliary wheels 7 is turning to the right-and-left relative to the straight moving direction of the base unit 3, the base unit 3 following the turning direction of the auxiliary wheels 7. Accordingly, a mobile X-ray imaging apparatus 1 according to the Embodiment 1 can be applied in the case of requiring a fine adjustment of the position of a base unit 3 in the fine movement mode with high accuracy.

Further, the mode discrimination element 31 sends the control signal after discriminating as the fine movement mode so that the movement calculation circuit 29 calculates the rotation rate of each drive wheel 5 as lower than that in the drive mode. Accordingly, the moving rate of the base unit 3 in the fine movement mode is lower than that in the drive mode. Accordingly, it can be prevented that the base unit 3 in the fine movement mode moves beyond the position intended by the operator and therefore the fine adjustment of the base unit 3 can be further facilitated.

Further, according to the Embodiment 1, the angle sensor 35 is configured to directly detect a turning angle of the auxiliary wheels 7 so that the data relative to further accurate turning angle of the auxiliary wheels 7 can be sent from the angle sensor 35 to the movement calculation circuit 29. Therefore, relative to the fine movement mode, the movement calculation circuit 29 can calculate the rotation direction and the rotation rate of the drive wheels 5 so as to change further accurately the turning angle of the auxiliary wheels 7 to the straight moving direction of the base unit 3. Accordingly, even when the auxiliary wheels 7 are turning to right and left relative to the straight moving direction of the base unit 3, the base unit 3 can be moved slightly and further accurately to the direction intended by the operator and the controllability of the mobile X-ray imaging apparatus 1 in the fine movement mode can be improved.

Further, the fine movement switch 23 is mounted to the collimator 17. Therefore, when the base unit 3 needs to be moved slightly while confirming the X-ray incident area by moving the X-ray tube 15 and the collimator 17, the base unit 3 can be slightly moved by operating the fine movement switch 23 at the operation site. Accordingly, the operator does not have to move all the way to the place where the drive handle 21 is present so that the X-ray imaging using the mobile X-ray imaging apparatus 1 can be performed further efficiently.

Further, according to the Embodiment 1, the mode discrimination element 31 discriminates the drive mode and the fine movement mode and is configured to switch the target to send the control signal respectively based on the discrimination results. Specifically, the mode discrimination element 31 discriminates that is a drive mode so that a control signal can be sent from the mode discrimination element 31 to the pressure sensor 33. As results, the rotation rate and the rotation direction of each drive wheel 5, which are calculated by the movement calculation circuit 29, are determined by the pressure detected by each pressure sensor 33.

On the other hand, when the mode discrimination element 31 discriminates the fine movement mode, the mode discrimination element 31 switches the target, to which the control signal is going to be sent, to the angle sensor 35. As results, the rotation rate and the rotation direction of each drive wheel 5, which are calculated by the movement calculation circuit 29, are determined according to the turning angle of the auxiliary wheels 7, which is detected by the angle sensor 35.

Targets, to which the mode discrimination element 31 sends the control signal, can be alternatively switched in each mode so that the data from the pressure sensor 33 and the angle sensor 35 cannot be sent to the movement calculation circuit 29 at the same time. Accordingly, it can be avoided that the control so as to turn the auxiliary wheels 7 to the straight moving direction of the base unit 3 is mistakenly performed in the drive mode. Further, an improper operation relative to the control mechanism in association with the drive mode in the fine movement mode can be prevented so that the position of the base unit can be more assuredly adjusted as intended in the fine movement mode.

Embodiment 2

Next, referring to FIGs, the inventors set forth the Embodiment 2 of the present invention. In addition, the inventor skips the detail description of the structure that is the same as the structure of a mobile X-ray imaging apparatus according to the Embodiment 1 but marking the same reference sign.

[Characteristic Structure Relative to Embodiment 2]

Figure 8:
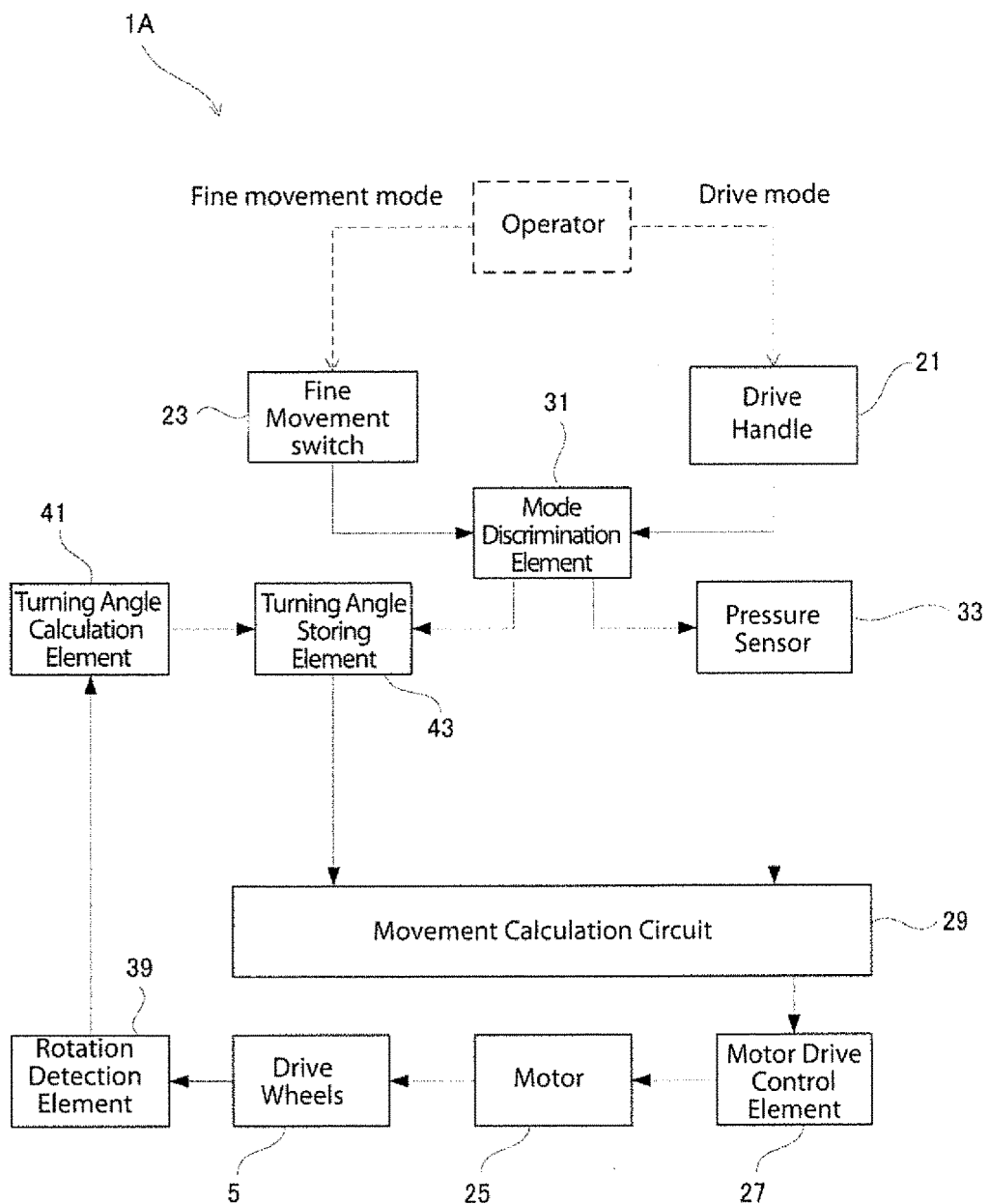
FIG. 8 is a functional block diagram illustrating the mobile X-ray imaging device of the Embodiment 2.

In addition, referring to FIG. 8, the mobile X-ray imaging apparatus 1A according to the Embodiment 2, a rotation detection element 39 is mounted to each drive wheel 5. The rotation detection element 39 detects the rotation rate and the rotation direction of the drive wheels 5 as needed and then sends the detected data to a turning angle calculation element 41. The turning angle calculation element 41 calculates the turning angle of the auxiliary wheels 7 relative to the base unit 3 based on the data related to the rotation rate and the rotation direction of the drive wheels 5 received from the rotation detection element 39. The rotation detection element 39 corresponds to the rotation detection means of the present invention.

As set forth above, the moving direction of the base unit 3 is determined based on the rotation rate and the rotation direction of the right and left drive wheels 5. Then, the turning direction of the auxiliary wheels 7 shifts based on the moving direction of the base unit 3 and the time period for which the moving direction is being maintained. For example, if the rotation rate of the left drive wheel 5 is faster than the rotation rate of the right drive wheel 5, the base unit 3 turns to the right direction and also the turning direction of the auxiliary wheels 7 shifts to the right direction. The longer time the base unit 3 is turning to the right direction, the larger turning angle of the auxiliary wheels 7 to the right direction is corresponding to the time thereof.

In such way, the turning angle calculation element 41 can calculate the turning direction and the turning angle of the auxiliary wheels 7 relative to the base unit 3 based on the rotation rate and the rotation direction of the right and left drive wheels 5 and the time period in which the rotation rate and the rotation direction of the right and left drive wheels 5 are being maintained. The turning angle calculation element 41 sends the calculated the turning angle of the auxiliary wheels 7 to the turning angle storing element 43 and then the turning angle storing element 43 stores the data related to the turning angle of the auxiliary wheels 7 as needed.

Then, the turning angle calculation element 43 sends the storing turning angle data to the movement calculation circuit 29 based on the control signal received from the mode discrimination element 31. The movement calculation circuit 29 calculates the rotation rate and the rotation direction of each drive wheel 5 respectively and sends the calculated data to the motor driving control element 27. The motor control element 27 controls drives of each motor 25 respectively based on the input data and rotates the respective drive wheels 5. Specifically, the turning angle calculation element 41 corresponds to the turning angle calculation means of the present invention and the turning angle storing element 43 corresponds to the turning angle storing means of the present invention.

(Fine Movement Mode According to the Embodiment 2)

The inventor sets forth the operation relative to the mobile X-ray imaging apparatus having the above described configuration according to the Embodiment 2. As the process of the operation according to the Embodiment 2 is the same as the process according to the Embodiment 1 but the Step 4, the inventor sets forth the fine movement mode relative to the Step S4.

When the position of the base unit 3 is adjusted in the fine movement mode of the mobile X-ray imaging apparatus 1A according to the Embodiment 2, the operator operates the fine movement switch 23. A signal is sent from the fine movement switch 23 to the mode discrimination element 31 by operating the fine movement switch 23. The mode discrimination element 31 discriminates the fine movement mode based on the received signal and sends the control signal to the angle storing element 43.

The turning angle storing element 43 stores the data received from the turning angle calculation element 41 as needed. The turning angle calculation element 41 calculates the turning angle of the auxiliary wheels 7 relative to the base unit 3 based on the data related to the rotation rate and the rotation direction of the respective drive wheels 5, which the rotation detection element 39 detects as needed. The turning angle of the auxiliary wheels 7 relative to the base unit 3 varies according to the moving direction of the base unit 3. Then, the moving direction of the base unit 3 is determined by the rotation rate and the rotation direction of the respective drive wheels 5. Accordingly, the turning angle calculation element 41 according to the Embodiment 2 is configured to be capable of calculating the turning angle of the auxiliary wheels 7 relative to the base unit 3 as needed based on the data that the rotation detection element 39 detects as needed. The turning angle storing element 43 stores the turning angle of the auxiliary wheels 7 relative to the base unit 3, which the turning angle calculation element 41 calculates at the end.

The turning angle storing element 43 sends the stored data related to the turning angle of the auxiliary wheels 7 to the movement calculation circuit 29 based on the control signal received from the mode discrimination element 31, by which the fine movement mode is discriminated. The movement calculation circuit 29 calculates the rate, direction and time to rotate the respective drive wheels 5 to turn the auxiliary wheels 7 quickly to the straight moving direction of the base unit 3 based on the received data relative to the turning angle of the auxiliary wheels 7.

The turning angle of the auxiliary wheels 7 relative to the base unit 3 varies according to the rotation rate difference between the right drive wheel 5 and the left drive wheel 5 and the variation thereof is determined by the rotation rate difference between the drive wheels 5 and the time period in which such difference is being maintained. Therefore, the movement calculation circuit 29 can calculate respectively the rotation rate and direction of the respective drive wheels 5, which is required to correct the turning direction of the auxiliary wheels 7 to the straight moving direction of the base unit 3 corresponding to the turning angle of the auxiliary wheels 7 relative of the base unit 3.

The data calculated by the movement calculation circuit 29 is sent to the motor driving control element 27 and the motor driving control element 27 controls the rotation rate of the respective motors 25 based on the received data. The respective drive wheels 5 rotate according to driving of the motor 25. Then, the turning direction of the auxiliary wheels 7 gradually turns to the straight moving direction of the base unit 3 according to the rotation rate difference between the right and left wheels 5. Then, the respective drive wheels 5 rotate for the constant time calculated by the moving calculation circuit 29 so that the auxiliary wheels 7 can turn accurately to the straight moving direction of the base unit 3. According to such fine movement mode, the base unit can be moved slightly in the straight moving direction at a low speed and the position of the base unit 3 can be adjusted to be in-place as intended.

(Effects of a Configuration According to the Embodiment 2)

A mobile X-ray imaging apparatus 1A according to the Embodiment 2 comprises a turning angle detection element 39, a turning angle calculation element 41 and a turning angle calculation storing element 43. The turning angle calculation element 41 is configured to calculate the turning angle of the auxiliary wheels 7 based on the rotation rate and the rotation direction of the drive wheels 5 detected by the rotation detection element 39. Then, the calculated data relative to the turning angle of the auxiliary wheels 7 are sent from the turning angle storing element 43 to the movement calculation circuit 29.

The movement calculation circuit 29 can calculate the rate, direction and time of rotation of the respective drive wheels 5, which are required to quickly correct the turning direction of the auxiliary wheels 7 so that the base unit 3 can move slightly in the straight moving direction, based on the turning angle of the auxiliary wheels 7. Then, the driving of the motors 25 is controlled based on the data calculated by the movement calculation element 29 so that the respective drive wheels 5 can rotate and the base unit 3 can slightly move in the straight moving direction, accordingly.

According to the mobile X-ray imaging apparatus 1A according to the Embodiment 2, the turning angle of the auxiliary wheels 7 is not directly detected, i.e., differently from the Embodiment 1, but the turning angle of the auxiliary wheels 7 can be calculated from the rotation rate and so forth of the drive wheels 5. Specifically, the calculation of the turning angle of the auxiliary wheels 7 is executed by means of the rotation detection element 39 having an encoder and so forth, the turning angle calculation element 41 as a software, and the turning angle storing element 43. Therefore, an angle sensor mounted to the auxiliary wheels 7 according to the Embodiment 1 is not needed. In addition, the conventional mobile X-ray imaging apparatus, as disclosed in Patent Document 2 and so forth, may be configured to have an encoder installed to drive wheels 5.

In such cases, a conventional apparatus, in which the turning angle calculation element 41 as software and the turning angle storing element 43 are additionally installed, has the structure according to the Embodiment 2. Specifically, no new hardware e.g., such as an angle sensor to be configured to calculate the turning angle of auxiliary wheels 7 in the fine movement mode, is not needed so that a mobile X-ray imaging apparatus 1A can be manufactured without any significant modifications as to the manufacturing processes and deign thereof. Accordingly, while the manufacturing cost for the mobile X-ray image apparatus 1A according to the Embodiment 2 is being saved, it can become controllable that the base unit slightly moves toward the straight moving direction in the fine movement mode.

Embodiment 3

Next, referring to FIGs., the inventors set forth the Embodiment 3 of the present invention. In addition, the inventor skips the detail description of the structure that is the same as the structure of a mobile X-ray imaging apparatus according to the Embodiment 1 but marking the same reference sign.

(Characteristic Structure Relative to Embodiment 3)

Figure 9:
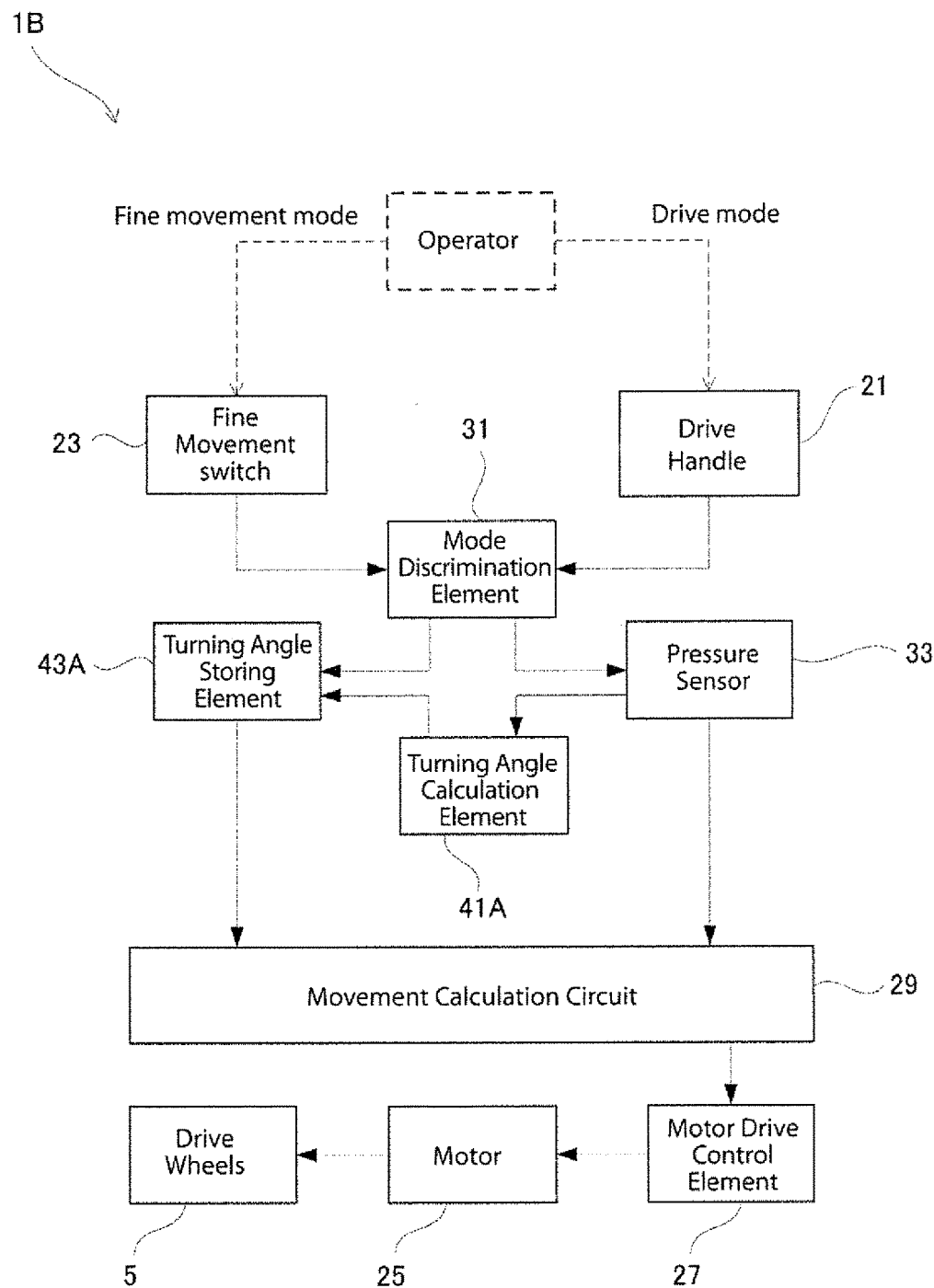
FIG. 9 is a functional block diagram illustrating the mobile X-ray imaging device of the Embodiment 3.
Figure 10:
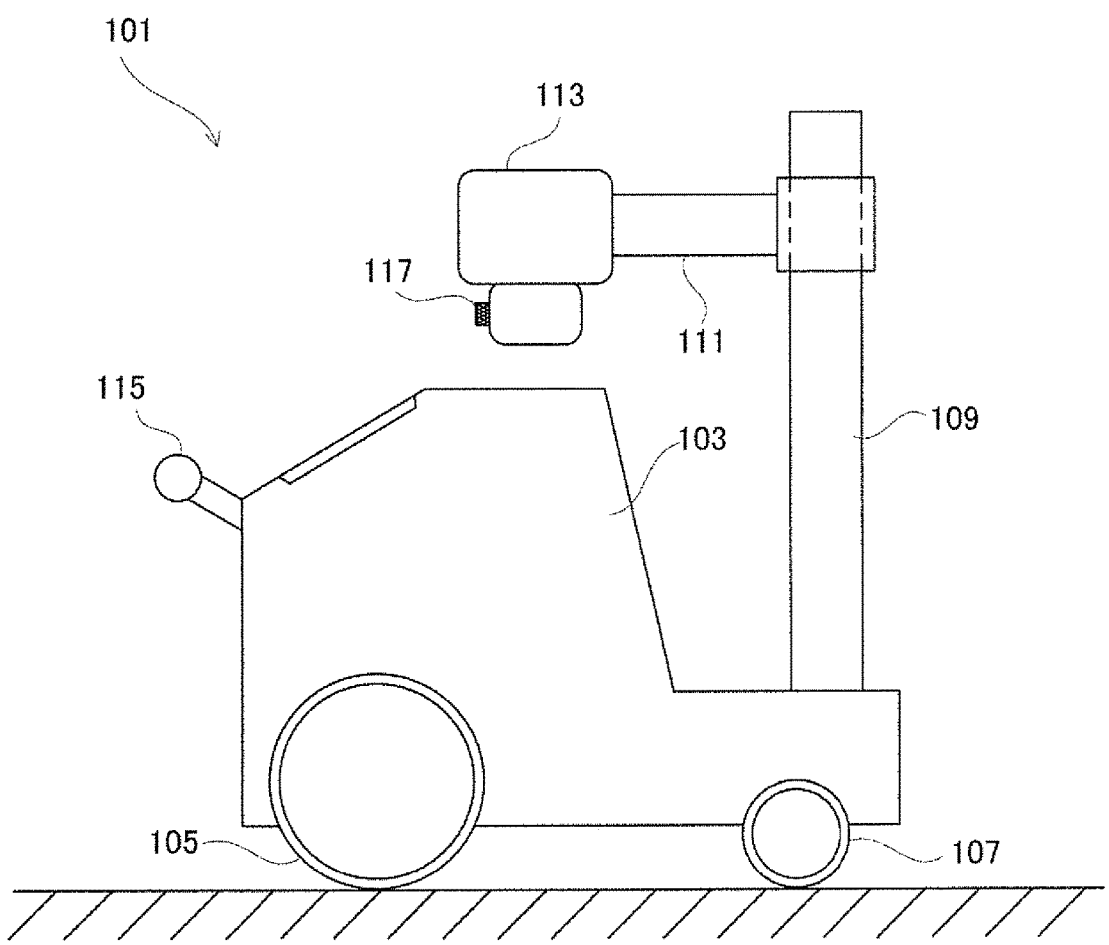
FIG. 10 is a left side view illustrating the structure of the mobile X-ray imaging apparatus of the conventional Example.
Figure 11:
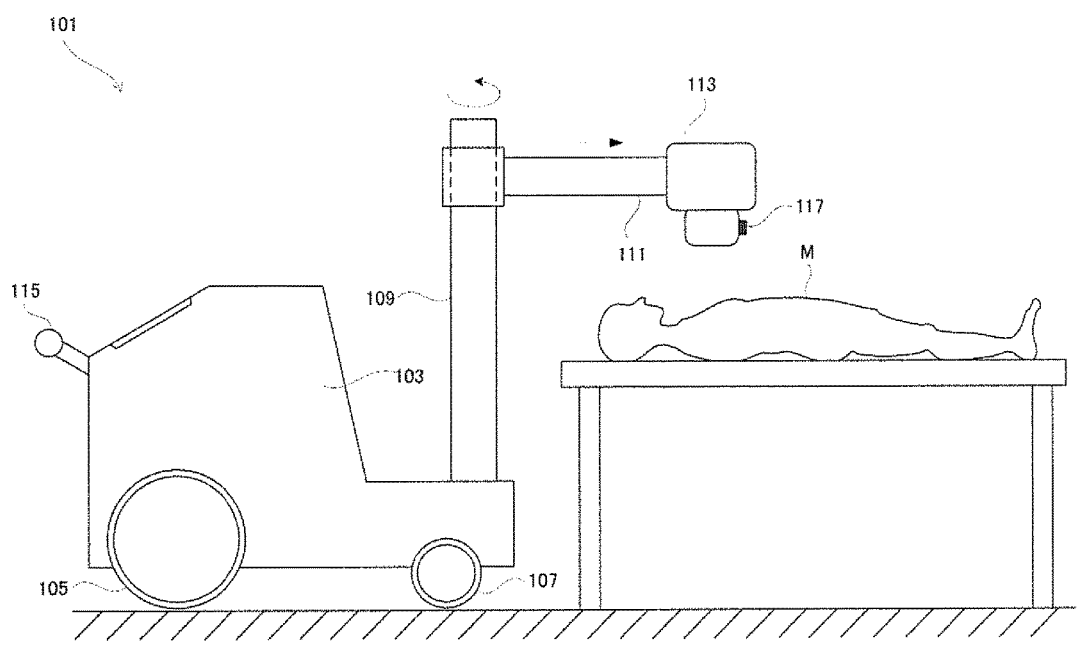
FIG. 11 is a left side view illustrating the operation of the mobile X-ray imaging apparatus of the conventional Example.
Figure 12:
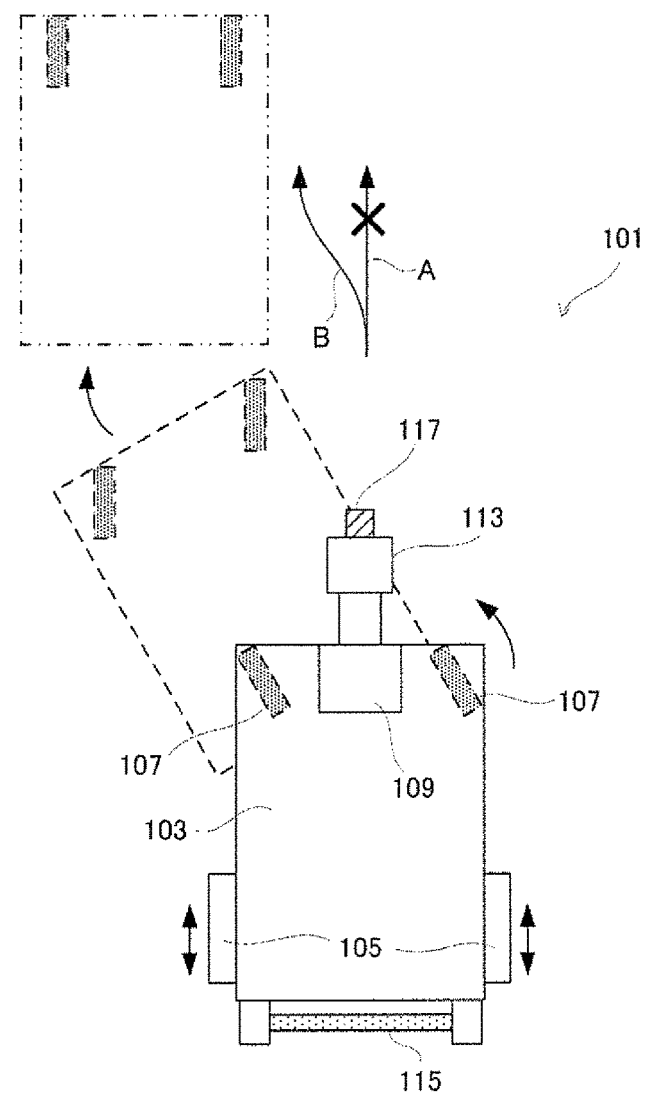
FIG. 12 is a plan view illustrating the problematic aspects of the mobile X-ray imaging apparatus of the conventional Example.

In addition, referring to FIG. 9, a mobile X-ray imaging apparatus 1B according to the Embodiment 3, a turning angle calculation element 41A is installed following the pressure sensor 33. The turning angle calculation element 41A calculates the turning angle of the auxiliary wheels 7 relative to the base unit 3 based on the data related to pressures detected by the respective pressure sensors 33.

Referring to FIG. 3(*b*), the moving direction of the base unit 3 is determined by which sensor among the pressure sensors 33*a*-33*d* detects the pressure in the driving mode. Then, the turning direction of the auxiliary wheels 7 shifts based on the moving direction of the base unit 3 and the time period at which the moving direction is being maintained. For example, if the pressure sensor 33*a* and the pressure sensor 33*d* detect the pressures, the base unit 3 turns to the right direction against the straight moving direction and also the turning direction of the auxiliary wheels 7 shifts to the right direction against the straight moving direction of the base unit 3. The longer the time period of detecting the pressure is, the larger the turning angle of the auxiliary wheels 7 to the right direction is corresponding to the time.

In such way, the turning angle calculation element 41A can calculate the turning direction and the turning angle of the auxiliary wheels 7 relative to the base unit 3 based on the combination of the pressure sensors 33*a*-33*d* detecting the pressure and the time while the pressure is being detected. The turning angle calculation element 41A sends the calculated the turning angle of the auxiliary wheels 7 to the turning angle storing element 43A and the turning angle storing element 43A stores the data related to the turning angle of the auxiliary wheels 7 relative to the base unit 3 as needed.

Then, each sensor 43A corresponds to the control signal received from the mode discrimination element 31 and sends the detected pressure data to the movement calculation circuit 29. A movement calculation circuit 29 is installed in the front part of the motor driving control element 27 and calculates the rotation rate and the rotation direction of each drive wheel 5 respectively. The motor control element 27 drives each motor 25 respectively based on the control signal and rotates each drive wheel 5.

(Fine Movement Mode According to the Embodiment 3)

The inventor sets forth the operation relative to the mobile X-ray imaging apparatus having the above described configuration according to the Embodiment 3. As the process of the operation according to the Embodiment 3 is the same as the process according to the Embodiment 1 and the Embodiment 2 but the Step 4, the inventor sets forth the fine movement mode relative to the Step S4.

When the position of the base unit 3 is adjusted in the fine movement mode in the mobile X-ray imaging apparatus 1B according to the Embodiment 3, the operator operates the fine movement switch 23. A signal is sent from the fine movement switch 23 to the mode discrimination element 31 by operating the fine movement switch 23. The mode discrimination element 31 discriminates the fine movement mode based on the received signal and sends the control signal to the angle storing element 43A.

The turning angle storing element 43A stores the data sent from the turning angle calculation element 41A as needed. The turning angle calculation element 41A calculates the turning direction of the auxiliary wheels 7 relative to the base unit 3 as needed based on the data related to pressures detected by the respective pressure sensors 33. The turning direction of the auxiliary wheels 7 relative to the base unit 3 varies according to the moving direction of the base unit 3. Then, referring to FIG. 3(b), the moving direction of the base unit 3 is determined based on the pressure data detected by the respective pressure sensors 33. Accordingly, the turning angle calculation element 41A according to the Embodiment 2 calculates the turning direction of the auxiliary wheels 7 relative to the base unit 3 based on the data related to pressures detected by the respective pressure sensors 33. The turning angle storing element 43A stores the turning direction of the auxiliary wheels 7 relative to the base unit 3 as needed, which the turning angle calculation element 41A calculates at the end.

The turning angle storing element 43A sends the stored data related to the turning direction of the auxiliary wheels 7 to the movement calculation circuit 29 based on the control signal sent from the mode discrimination element 31, which is discriminated as the fine movement mode. The movement calculation circuit 29 calculates the rate of rotating, the direction and time relative to the drive wheels 5 to quickly correct the turning direction of the auxiliary wheels 7 to the straight moving direction based on the received data relative to the turning direction of the auxiliary wheels 7 as wells as according to the Embodiment 2. The calculated data is sent to the motor driving control element 27 and the motor driving control element 27 controls the driving of the respective motors 25 based on the data that are calculated by the movement calculation circuit 29.

The respective drive wheels 5 rotate according to driving of the motor 25. Then, the turning direction of the auxiliary wheels 7 relative to the base unit 3 is changed quickly to the straight moving direction by being maintained the difference of the rotation rate of the right-and-left drive wheels 5 for a constant time. According to such fine movement mode, the base unit can be moved slightly in the straight moving direction at a low speed and the position of the base unit 3 can be adjusted to be in-place as intended.

(Effects of the Configuration According to the Embodiment 3)

A mobile X-ray imaging apparatus according to the Embodiment 3 comprises a turning angle calculation element 41A and a turning angle storing element 43A. The turning angle calculation element 41A calculates the turning angle of the auxiliary wheels 7 at the present time based on the data detected by the respective pressure sensors 33. Then, the calculated data relative to the turning angle of the auxiliary wheels 7 are sent from the turning angle storing element 41A to the movement calculation circuit 29. The movement calculation circuit 29 can calculate the rotation rate and the rotation direction of the respective drive wheels 5, which are required to quickly correct the turning direction of the auxiliary wheels 7 so that the base unit 3 can move slightly in the straight moving direction, based on the turning angle of the auxiliary wheels 7 relative to the base unit 3. Then, the driving of the motors 25 is driven based on the calculated data so that the respective rotations of drive wheels 5 can be controlled as the base unit 3 can slightly move in the straight moving direction, accordingly.

When the fine movement switch 23 is operated to finely adjust the position of the base unit 3, the turning angle of the auxiliary wheels 7 relative to the base unit 3 is as the turning angle when the move to the patient's room in the drive mode is completed. The turning angle of the auxiliary wheels 7 relative to the base unit 3 varies according to the turning direction of the base unit 3. Then, the turning direction of the base unit 3 is determined based on the pressure data detected by the respective pressure sensors 33. Therefore, the turning angle calculation element 41A can calculates accurately the turning angle of the auxiliary wheels 7 based on the data detected by the respective pressure sensors 33 when the fine movement switch 23 is operated.

According to the mobile X-ray imaging apparatus according to the Embodiment 3, the turning angle of the auxiliary wheels 7 is not directly detected differently from that in the Embodiment 1, but the turning angle of the auxiliary wheels 7 can be calculated from the pressure data detected by the respective sensors 33. Then, the calculation of the turning angle of the auxiliary wheels 7 is executed by means of the turning angle calculation element 41A as software, and the turning angle storing element 43A. Therefore, a mobile X-ray imaging apparatus according to the Embodiment 1 needs additionally no new hardware, e.g., such as an angle sensor, to be configured to calculate the turning direction of auxiliary wheels 7 in the fine movement mode. Accordingly, any significant modifications of the manufacturing processes and designs as to the mobile X-ray image apparatus 1B according to the Embodiment 3 are not required so that an cost increase relative to manufacturing can be avoided and it can become controllable that the base unit slightly moves toward the straight moving direction in the fine movement mode.

The present invention is not limited to the aspect of the Embodiments set forth above, and further another alternative Embodiment can be implemented set forth below.

(1) According to each Embodiment set forth above, a pair of drive wheels 5 is configured to be mounted to the rear-bottom part of the base unit 3 and a pair of the auxiliary wheels 7 is configured to be mounted to the front-bottom of the base unit 3, but not limited thereto. Specifically, the position and the number of the drive wheels 5 and the auxiliary wheels 7 can be modified as desired.

(2) According to the Embodiment 1 set forth above, the mode discrimination element 31, which discriminates the fine movement mode, is configured to control the data transmission from the angle sensor 35 to the movement calculation circuit 29, but it can be configured to control the operation per se of the angle sensor 35. Specifically, the angle sensor 35 is configured to detect the turning direction of the auxiliary wheels 7 based on the control signal that the mode discrimination element 31 would send.

(3) According to the Embodiment 2 set forth above, the mode discrimination element 31, which discriminates the fine movement mode, is configured to control the data transmission from the angle storing element 43 to the movement calculation circuit 29, but it is not limited thereto. Specifically, the rotation detection element 39 is configured to detect the rotation rate of the drive wheels 5 based on the control signal that the mode discrimination element 31 would send. Further, the turning angle calculation element 41 is configured to calculate the turning angle of the auxiliary wheels 7 relative to the base unit 3 based on the control signal that the mode discrimination element 31 would send.

(4) According to the Embodiment 3 set forth above, the mode discrimination element 31, which discriminates the fine movement mode, is configured to control the data transmission from the angle storing element 43A to the movement calculation circuit 29, but it is not limited thereto. Specifically, the turning angle calculation element 41A is configured to calculate the turning angle of the auxiliary wheels 7 based on the control signal that the mode discrimination element 31 would send.

REFERENCE OF SIGN

1 Mobile X-ray imaging apparatus
3 Base unit
5 Drive wheel
7 Auxiliary wheel
15 X-ray tube (Radiation source)
17 Collimator
21 Drive handle (Drive operation means)
23 Fine movement switch (Fine movement instruction means)
25 Motor
27 Motor drive control element
29 Movement calculation circuit
31 Mode discrimination element (Mode discrimination means)
35 Angle sensor
39 Rotation detection element (Rotation detection means)
41 Turning angle calculation element (Turning angle calculation means)
43 Turning angle storing element (Turning angle storing means)

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A mobile X-ray imaging apparatus, comprising:
a base unit mounting an X-ray tube;
a pair of drive wheels that is installed to said base unit and moves the base unit straight and turns the base unit and are being driven independently from each other;
auxiliary wheels that are installed to the base unit and turn following a turning movement of said base unit,
a drive operation means that has an operation handle and conducts an operation of said base unit in a drive mode, wherein the pair of drive wheels can be rotated independently of each other to move the base unit straight and turn the base unit based on an operation force added to the operation handle;
a fine movement instruction means that specifies the movement of the base unit according to a fine movement mode,
wherein said base unit is moved straight by rotating said drive wheels at the lower rotation rate than the rotation rate in said drive mode;
a turning angle detection means that detects a turning angle of said auxiliary wheels relative to the straight moving direction of said base unit;
a drive wheel control means that controls the rotation rates of said pair of drive wheels independently each other,
wherein said auxiliary wheels turn to the straight moving direction of said base unit based on the turning angle of said auxiliary wheels, which is detected by said turning angle detection means in the fine movement mode.

2. The mobile X-ray imaging apparatus, according to claim 1 wherein:
said angle detection means is an angle sensor that detects a turning angle of said auxiliary wheels relative the straight moving direction of said base unit.

3. The mobile X-ray imaging apparatus according to claim 1, wherein:
said turning angle detection means, further comprises:
a turning angle calculation circuit that calculates a turning angle of said auxiliary wheels relative to the straight moving direction of said base unit as needed, and
a turning angle storing circuit that stores the turning angle, calculated as needed by said turning angle calculation circuit, of said auxiliary wheels relative to the straight moving direction of said base unit; and
wherein said drive wheel control means that controls rotation rates of the pair of the drive wheels independently each other as said auxiliary wheels turn to the straight moving direction of said base unit based on the turning angle that is stored by said turning angle storing circuit.

4. The mobile X-ray imaging apparatus according to claim 3, further comprising:
a rotation detection circuit that detects a rotation rate and a rotation direction of said drive wheels as needed; and
wherein said turning angle calculation means calculates a turning angle of said auxiliary wheels relative to the straight moving direction of said base unit based on the rotation rate and the rotation direction of said drive wheels detected by said rotation detection means as needed.

5. The mobile X-ray imaging apparatus according to claim 3, wherein:
said turning angle calculation circuit calculates a turning angle of said auxiliary wheels relative to the straight moving direction of said base unit based on the pressure detected by an angle sensor installed to said drive handle.

6. The mobile X-ray imaging apparatus according to claim 1, further comprising:
a mode discrimination circuit that discriminates a drive mode and a fine movement mode, and switches the on-and-off control of rotation rates of said pair of drive wheels by said drive wheel control means based on the discrimination result.

7. The mobile X-ray imaging apparatus according to claim 5, further comprising:
a mode discrimination circuit that discriminates a drive mode and a fine movement mode, and switches the on-and-off control of rotation rates of said pair of drive wheels by said drive wheel control means based on the discrimination result.

* * * * *